United States Patent [19]

McNally

[11] Patent Number: 5,814,574
[45] Date of Patent: *Sep. 29, 1998

[54] CATALYST COMPOSITIONS AND PROCESS FOR PREPARING POLYOLEFINS

[75] Inventor: John Paul McNally, Berkshire, United Kingdom

[73] Assignee: BP Chemicals Limited, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 689,191

[22] Filed: Aug. 5, 1996

Related U.S. Application Data

[63] Continuation of Ser. No. 179,933, Jan. 11, 1994, abandoned.

[30] Foreign Application Priority Data

Jan. 19, 1993 [GB] United Kingdom .................. 9300934

[51] Int. Cl.⁶ .................................................. B01J 31/12
[52] U.S. Cl. ..................... 502/103; 502/117; 502/132; 502/152; 502/156; 556/51
[58] Field of Search .................... 502/156, 152, 502/132, 117, 103; 556/51

[56] References Cited

U.S. PATENT DOCUMENTS

| | | | |
|---|---|---|---|
| 4,639,430 | 1/1987 | Pasquet et al. | 502/120 |
| 5,026,798 | 6/1991 | Canich | 526/127 |
| 5,057,475 | 10/1991 | Canich et al. | 502/104 |
| 5,122,491 | 6/1992 | Kioka et al. | 502/117 |
| 5,126,301 | 6/1992 | Tsutsui et al. | 502/108 |
| 5,227,440 | 7/1993 | Canich et al. | 526/129 |
| 5,234,878 | 8/1993 | Tsutsui et al. | 502/103 |
| 5,266,544 | 11/1993 | Tsutsui et al. | 502/113 |
| 5,276,208 | 1/1994 | Winter et al. | 556/53 |
| 5,475,075 | 12/1995 | Brant et al. | 526/348.3 |

OTHER PUBLICATIONS

Chemical Abstract 111:233037 based on article to Wei et al., Transition Met. Chem. (London), 14(4), 315–18, no month, 1989.

Sax et al. "Hawley's Condensed Chemical Dictionary", 11th Ed., Van Nostrand Reinhold, New York (1987) pp. 697–698 (no month).

Wei et al. "Chinese Journal of Reactive Polymers" 1(2), pp. 122–131 (1992) (no month).

Burger et al., "Organometallics", 11, pp. 1319–1327 (1992) (no month).

Qichen et al. "Organotitanium Chemistry 12. Synthesis of some new chiral cyclopentadienyl titanium and zirconium complexes". Transition of Met. Chem., 14, 315–318 (1989). (no month).

Wei et al. "Synthesis and Reactions of Bis(beta–Alkoxy–Etheyl Cyclopentadienyl) Titanium and (Zirconium) Dichlorides". Chinese Journal of Reactive Polymers. 1(2) 122–131. (1992). (no month).

*Primary Examiner*—Shrive Beck
*Assistant Examiner*—Timothy Meeks
*Attorney, Agent, or Firm*—Brooks Haidt Haffner & Delahunty

[57] ABSTRACT

A catalyst composition comprising at least one metallocene complex of general formula I or II $$M[X(R)_n]_x Y_p \qquad (I)$$

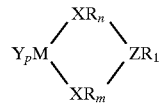

wherein R is a univalent of divalent 1–20c hydrocarbyl, or a 1–20c hydrocarbyl containing substituent oxygen, silicon, phosphorus, nitrogen of sulphur atoms with the proviso that at least one R group contains a lewis base functionality and when there are two or more R groups present they may be the same or different, and when R is divalent it is directly attached to M and replaces a Y ligand, and wherein M is a Group IVA metal, Y is a univalent anionic ligand X is an organic group containing a cyclopentadienyl nucleus and for formula I n is an integer of 1 to 10 x is either 1 or 2, and for formula II, n, m and l are integers or 0 such that $n+m+l \geq 1$, $p = 0-2$, and z is a $c_1$ to $c_4$ alkylene radical or a dialkyl germanium or silicon or an alkyl phosphine or amine radical or bis-dialkylsilyl or bis-dialkylgermanyl containing hydrocarbyl groups having 1 to 4 carbon atoms bridging the cyclopentadienyl nuclei.

15 Claims, 2 Drawing Sheets

FIG.1 Examples for Metallocenes of Formula I.
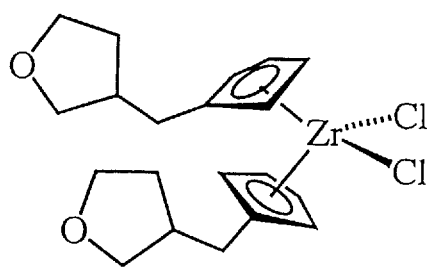
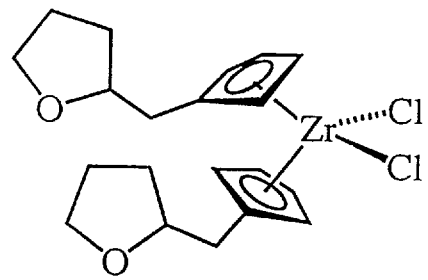
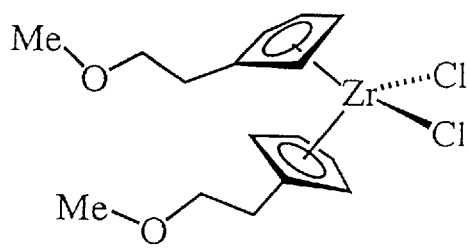
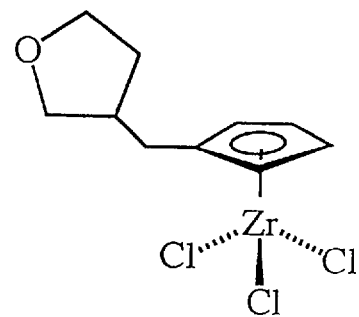
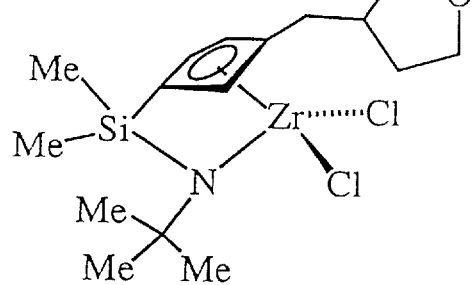
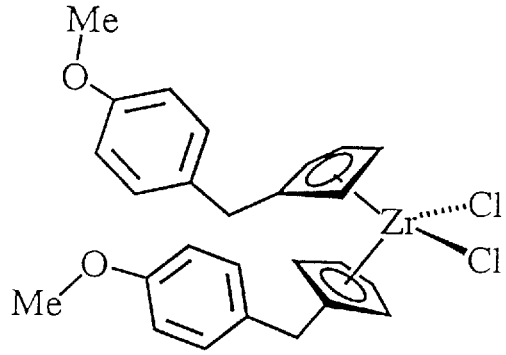
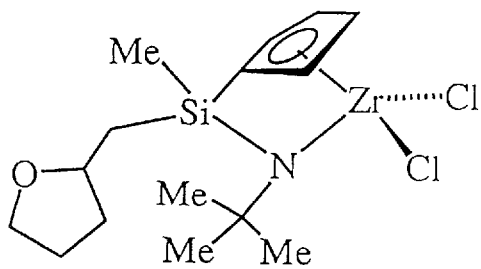
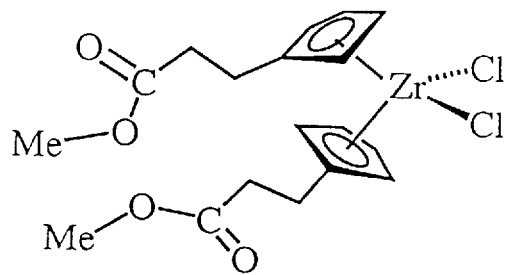

FIG. 2 Example for Metallocenes of Formula II.
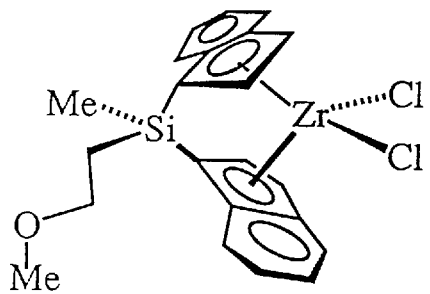
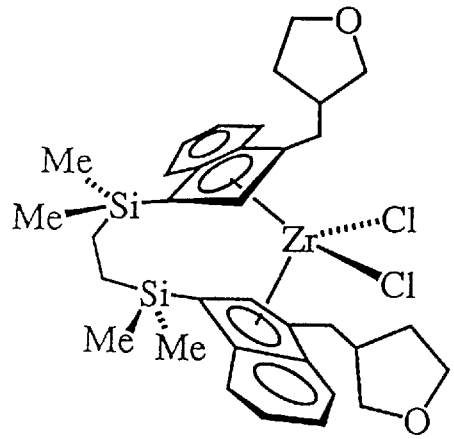
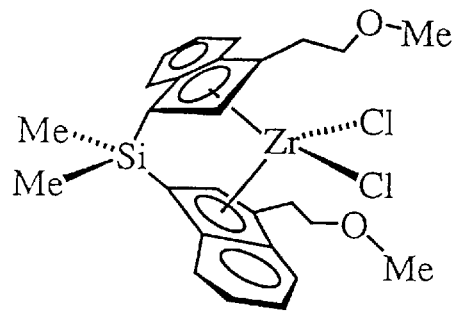
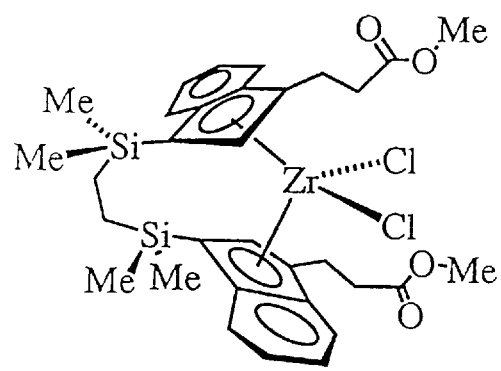
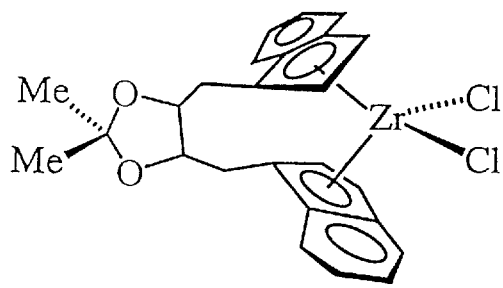
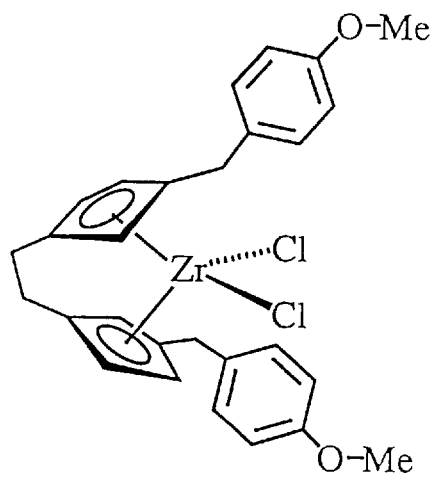

CATALYST COMPOSITIONS AND PROCESS FOR PREPARING POLYOLEFINS

This application is a continuation, of application Ser. No. 08/179,933, filed Jan. 11,1994, now abandoned.

BACKGROUND OF THE INVENTION

The present invention relates to novel catalyst compositions comprising metallocene complexes and their use in the polymerisation of olefins.

Metallocene complexes of Group IVA metals such as (cyclopentadienyl)$_2$ZrCl$_2$ are known as homogeneous polyolefin catalysts when used in the presence of a suitable co-catalyst. Such catalyst systems have proven to be highly active towards ethylene and alpha olefins forming narrow molecular weight distribution polyolefins.

It would be highly desirable to provide catalyst compositions which may be used, particularly in the gas phase, to provide greater flexibility in the range of polymers produced.

We have now discovered a group of metallocene complexes comprising at least one specific Lewis base functionality. Such complexes may be used in the polymerisation of olefins.

SUMMARY OF THE INVENTION

Accordingly, the present invention provides a catalyst composition comprising at least one metallocene complex of the general formula I or II $$M[X(R)_n]_xY_p \quad (I)$$

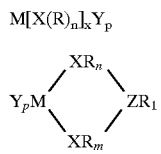

wherein R is a univalent or divalent 1–20C hydrocarbyl, or a –20C hydrocarbyl containing substituent oxygen, silicon, phosphorus, nitrogen or sulfur atoms with the proviso that at least one R group contains a Lewis base functionality and when there are two or more R groups present they may be the same or different, and when R is divalent it is directly attached to M, and replaces a Y ligand, wherein M is a Group IVA metal, Y is a univalent anionic ligand, X is an organic group containing a cyclopentadienyl nucleus and for formula I n is an integer of 1 to 10 x is either 1 or 2, and when x =1, p =0 –3, that is, when all R are univalent, p =3; when one R is divalent, p =2; when two Rs are divalent, p =1 and when three Rs are divalent, p =0, when x =2, p =0 –2, that is when all R are univalent, p =2; when one R is divalent, p =1; when two Rs are divalent, p =0, and for formula II, n, m and l are integers or 0 such that n +m +l $\geq$1, p =0 –2, that is, when all R are univalent, p =2; when one R is divalent, p =1; when two Rs are divalent, p =0, and Z is a C$_1$ to C$_4$ alkylene radical or a dialkyl germanium or silicon or an alkyl phosphine or amine radical or bis-dialkylsilyl or bis-dialkylgermanyl containing hydrocarbyl groups having 1 to 4 carbon atoms bridging the cyclopentadienyl nuclei.

DESCRIPTION OF THE PREFERRED EMBODIMENTS

The metallocene complex of the present invention is a Group IVA metallocene of general formula I or II wherein M is suitably hafnium, zirconium or titanium. Preferably M is zirconium.

In the metallocene complex of general formula I or II, X comprises a cyclopentadienyl nucleus. Suitably X represents a single ring cyclopentadienyl nucleus or a fused ring one such as indenyl or tetrahydroindenyl or fluorenyl nucleus.

At least one R contains one or more Lewis base functionalities. By a "Lewis base functionality" is meant a functional group with at least one donatable electron pair. Suitable examples of Lewis base functionalities include alcohols, ethers, carboxylic acid esters, amino groups, and their second row analogues. By second row analogue is meant the corresponding phosphorus or sulfur group. Where R is divalent, and replaces a Y ligand, it may also contain a Lewis Base functionality additional to the moiety directly attached to the metal M. The functionality may be attached to the moiety, or elsewhere within R. Where R is divalent and does not contain an additional Lewis Base functionality, there must be more than one R group present in the complex to ensure that at least one Lewis Base functionality is present which is not directly attached to the metal M.

Where R contains an alcohol, an ether, an amine, a phosphine, a thiol, or a thioether group, suitably R is of general formula III $$-(R^2)_q-W \quad (III)$$

where q is 0 or an integer, e.g. 1–4, preferably 1. R$^2$ is a divalent hydrocarbyl group having 1 to 20 carbon atoms. Suitably R$^2$ may be an alkylene having 1 to 6 carbon atoms, e.g. 1,2 ethylene, 1,2 or 1,3propylene or a cycloalkylene of suitably 5 to 7 carbon atoms or an aromatic hydrocarbyl of 6 to 20 carbon atoms. For an alcoholic functionality, W is —OH; for an ether functionality, W is —OR$^3$; for an amine functionality, W is —NR$^4$R$^5$; for a phosphine functionality, W is —PR$^6$R$^7$; for a thiol functionality, W is —SH; for a thioether functionality, W is —SR$^8$.

R$^3$–R$^8$ are monovalent hydrocarbyl groups of suitably 1 to 20 carbon atoms such as an alkyl group, for example methyl or ethyl or a cycloalkyl group, e.g. cyclohexyl groups or aromatic hydrocarbyl, e.g. phenyl. One or more of R$^4$–R$^7$ may also be H. R$^3$–R$^8$ may also contain aditional Lewis basic functionalities, for example when W is —OR$^3$,R$^2$ could be —CH$_2$CH$_2$—, and R3 could be the polyether group —(CH$_2$CH$_2$O)$_n$—CH$_3$, where n is 1–6, preferably 3.

Examples of suitable ether groups are 3-alkoxy alkylene and 2-alkoxy alkylene such as 2-methoxy or 2 ethoxy ethylene or alkoxy phenyl ether. The analogous sulfur thio ether groups may also be used.

Furthermore, R$^2$ may be a trivalent hydrocarbyl group and together with one of R$^3$–R$^8$ may form a ring saturated or unsaturated of suitably 4 to 6 carbon atoms for bonding to X directly as in tetrahydro-3-furanmethyl or tetrahydro-2-furanmethyl. Analogous sulphur thio ether groups, cyclic amino, or cyclic phosphido groups may also be used.

Where R of general formula I or II is a carboxylic acid ester group, suitable groups may be of general formula IV or V

wherein R$^9$ and R$^{11}$ are independently a divalent hydrocarbyl group, for example, as described for R$^2$ above, especially methylene and ethylene. $R^{10}$ and $R^{12}$ are independently a hydrocarbyl group, for example, as described for $R^3$–$R^8$ above, especially an alkyl group of 1 to 10 carbon atoms such as methyl or ethyl. Examples of such ester groups are alkoxycarbonylalkylene such as ethoxy carbonylethylene and alkanoyloxymethylene such as acetoxy-methylene or ethylene. $R^{10}$ and $R^{12}$ may also contain additional Lewis basic functionalities.

Furthermore, $R^9$ or $R^{11}$ may be a trivalent hydrocarbyl group and together with $R^{10}$ or $R^{12}$ respectively may form a cyclic ester or lactone.

Y in general formula I or II is a univalent anionic ligand. Suitably, the ligand is selected from hydrogen; halides, e.g. chloride or bromide; unsubstituted hydrocarbyls, e.g. of 1 to 10 carbon atoms such as methyl or ethyl; alkoxide such as ethoxides or methoxide; amide or phosphide, e.g. a dialkylamide or a dialkyl or alkyl aryl phosphide group with 1 to 10 carbon atoms in each alkoxide or alkyl group in Y and 6 to 20 carbon atoms in the aryl group.

The preferred metallocene complex of general formula I is when:

M is zirconium

R is an ether group or a thioether group

X is a cyclopentadienyl group

Y is chloride, n is 1 or 5, and x is 2, and p is 2.

The most preferred metallocene complex is when R is tetrahydro-3-furanmethyl in particular the complex having the formula:

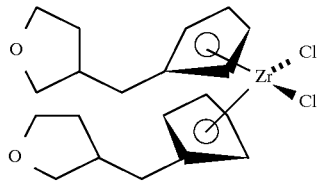

The preferred metallocene complex of general formula II is when:

M is zirconium

R is an ether group or a thioether group

X is an indenyl group

Y is chloride n =m =1 l =0, and

Z is a $C_1$ to $C_4$ alkylene or a bis-dimethylsilyl containing $C_1$ to $C_4$ hydrocarbyl group.

The most preferred metallocene complex is when R is tetrahydro-3-furanmethyl.

BRIEF DECRIPTION OF THE DRAWINGS

Examples of suitable metallocene complexes of general formula I and general formula II are illustrated in the attached FIGS. 1 and 2 respectively.

The metallocene complexes of general formula I where X=2, and general formula II may suitably be prepared by reacting a suitable group IVA metal salt of the general formula $MY_2Cl_2$ with a cyclopentadienyl anion of the general formula $[X(R_n)]M^2$ or $[X(R)_n—ZR_1—X(R)_m]M^2{}_2$, where $X(R_n)$ is defined previously. Suitably $M^2$ is a cation of a Group I metal, preferably Li, Na or especially K. It is preferred that the group IVA metal salt is a tetrahalide salt, most preferably the tetrachloride salt. It is preferred that the preparation of the metallocene complex is carried out in the presence of an anhydrous organic solvent such as an aliphatic ether, e.g. diethyl ether or an aromatic hydrocarbon such as toluene or a cyclic ether, e.g. tetrahydrofuran and under dry nitrogen. The preferred conditions are in the presence of tetrahydrofuran and under nitrogen.

The salts of general formula $[(X(R_n)]M^2$ and $[X(R)_n—ZR_1—X(R)_m]M^2{}_2$ may be prepared by any suitable method from the corresponding compounds of formula $X(R_n)H$ and $[X(R)_nH—ZR_1—X(R)_mH]$ by reaction with a suitable metal or organo hydrocarbyl metal compound. Suitably the metal is a Group I metal selected from lithium, sodium, or potassium. The organo hydrocarbyl metal compound is suitably an organo hydrocarbyl alkali metal compound such as an alkyl or phenyl lithium, sodium, or potassium compound, preferably a lithium compound.

The compound $X(R_n)H$ may itself be formed by reaction of a compound of general formula $[X(R_{n-1})H]M^3$ with R–R" where $M^3$ is an alkali metal, R is as defined above and R" is a suitable leaving group under nucleophilic conditions. For example, R–R" may be tetrahydro-3-furanmethylbromide or tetrahydro-3-furanmethyltosylate. Additional groups of general formula R may be added to the cyclopentadienyl nucleus through repetition of this procedure. Alternatively, $[X(R_n)H]M^3$ and $[X(R_m)H]M^3$ may be reacted with $ZR_1R"_2$ to form $[X(R)_nH—ZR_1—X(R)_mH]$.

Where it is desired to prepare the metallocene complex of general formula I wherein x is 1, the complex may suitably be prepared using procedures where typically, the cyclopentadiene compound $X(R)_nH$ would be reacted with a metallating agent where the metal ($M^4$) is a group I alkali metal to provide $X(R)_nM^{4\cdot}$ Metallating agents include K, n-BuLi or MeLi. Suitably $X(R)_nM^4$ is then reacted with trimethylsilyl chloride in an appropriate solvent to provide $(Me_3Si)X(R)_n$. Further reaction with a group IVA metal salt, for example the metal halide, will suitably provide a metallocene complex of general formula $M[X(R)_n]Y_3$. This synthesis is particularly preferred for the preparation of monocyclopentadienyl titanium complexes.

If desired, the complex of general formula I wherein Y is halide may be converted into the complex of general formula I wherein Y is another specified group by reaction of the halide with an appropriate nucleophile, e.g. an alkoxide.

One or more metallocenes of general formula I or II may suitably be supported on an inorganic support to give a catalyst composition which forms one aspect of the present invention. Suitably, the supported metallocene complex of general formula I or II comprises from 0.05 to 50% w/w of the catalyst composition. Any suitable inorganic support may be used, for example, inorganic oxides such as silica, alumina, silica-alumina mixtures, thoria, zirconia, magnesia, titania and mixtures thereof. Suitably, inorganic halides may be used. Suitable halides include group II halides, e.g. magnesium chloride.

One or more metallocene complexes of general formula I or II may also be supported on a support which has been impregnated with a Lewis acid. Suitable Lewis acids include Group VA, VIA halides, Group III, IV, VB halides and hydrocarbyl halides. Examples of such Lewis acids are $BF_3$, $BCl_3$, $AlCl_3$, $AlEtCl_2$, $AlEt_2Cl$, $PCl_3$ and $PCl_5$.

Additionally, one or more metallocene complexes of general formula I or II may be supported on a component which itself may have polymerisation activity, to give a catalyst composition which comprises another aspect of the present invention. Suitably the metallocenes may be supported on a supported olefin polymerisation catalyst, especially where the support is magnesium chloride or silica. Suitably, supported Ziegler catalysts may be used to support one or more metallocene complexes. Other suitable supported olefin polymerisation catalysts may be prepared from precursors which include $VCl_4$, $VCl_3$, $VCl_2$, $NbCl_5$, $TaCl_5$, $CrCl_3$, $CrCl_2$, $MoCl_5$, $WCl_5$, $TiCl_4$, $TiCl_3$ and $ZrCl_4$. Such supported olefin polymerisation catalysts are well known and their preparation are well described in the literature.

The metallocene complexes of general formula I or II may suitably be impregnated onto the support material under anhydrous conditions and under an inert atmosphere.

Suitably, catalyst compositions of the present invention may be mixed with a co-catalyst. Suitable co-catalysts include organometallic compounds of a metal of Group I, II or III of the periodic table, especially IA, IIA or B, IIIB. Preferably, the metals are selected from the group including lithium, aluminium, magnesium, zinc and boron. Such co-catalysts are known for their use in polymerisation reactions, especially the polymerisation of olefins, and include organo aluminium compounds such as trialkyl, alkyl hydrido, alkylhalo and alkyl alkoxy aluminium compounds. Suitably each alkyl or alkoxy group contains 1–16 carbons. Examples of such compounds include trimethyl aluminium, triethylaluminium diethyl aluminium hydride, triisobutyl aluminium, tridecyl aluminium, tridodecyl aluminium, diethyl aluminium methoxide, diethyl aluminium ethoxide, diethyl aluminium phenoxide, diethyl aluminium chloride, ethyl aluminium dichloride, methyl diethoxy aluminium and methyluminoxane. The preferred compound is an alkyl aluminoxane, the alkyl group having 1 to 10 carbon atoms, especially methyl aluminoxane. Where Y of general formula I or II is hydrogen or hydrocarbyl, suitable co-catalysts also include Bronsted and Lewis acids.

The co-catalyst may simply be mixed with the catalyst composition. Alternatively, the co-catalyst may be added to the polymerisation medium along with the catalyst composition. Suitably, the amount of co-catalyst mixed with the metallocene complex may be such as to provide an atom ratio of M from the metallocene to the metal in the co-catalyst of 1–10,000:10,000–1 for aluminoxanes and 1–100:100–1 for other co-catalysts.

It is a particular advantage of this invention that an active catalyst composition comprising a metallocene complex may be supported on an inorganic oxide or metal halide without using cocatalysts such as aluminoxanes as the means of support. Aluminoxanes are expensive and difficult to handle and it is desirable to minimise their use. Conventionally, they are used both as a means of binding metallocenes to inorganic supports and as cocatalysts. The current invention obviates the need for aluminoxanes as a means of binding. This allows their use as cocatalysts only or not at all by selecting alternative cocatalysts, eg. Bronsted or Lewis Acids.

The catalyst composition of the present invention in the presence of a co-catalyst may be used as a catalyst in the polymerisation of olefins or may suitably be used to prepare a prepolymer which may then be used as a catalyst in the polymerisation reaction. The prepolymer is a catalytically active polymer. The prepolymer is usually a mixture of a low yield polymer and the catalyst.

Where it is desired to use a prepolymer in the polymerisation reaction, the catalyst prepolymer may suitably be prepared by heating an olefin in the presence of a catalyst composition of the invention usually in the presence of an inert solvent and/or a suitable co-catalyst, as detailed herein before.

The polymerisation process comprises contacting the monomer or monomers, optionally in the presence of hydrogen, with the catalyst composition, and in the presence of a co-catalyst at a temperature and pressure sufficient to initiate the polymerisation reaction.

Where the polymerisation reaction is carried out using a catalyst composition comprising two or more metallocene complexes of general formula I or II or at least one metallocene complex of general formula I or II supported on a support capable of showing polymerisation activity, there may suitably be at least two classes of active site. If desired, both active sites may be retained during the olefin polymerisation reaction to provide a final polymer comprising polyolefins with differing molecular weight and/or branch distribution. Such polymers may have a bimodal molecular weight distribution. Alternatively, one active site in the catalyst composition, in particular the active site due to the non-metallocene catalyst, may be deactivated or not activated prior to use in the polymerisation reaction, the resulting polyolefin having a uniform molecular weight and/or branch distribution due to the metallocene component alone. The latter option may be achieved by, for example, selectively deactivating the active site of the non-metallocene catalyst by chemical treatment or choosing a non-metallocene catalyst and/or conditions which give rise to very low polymerisation activity relative to that of the metallocene sites. Alternatively, the relative proportions of the two catalytically active components of the prepolymer composition may be chosen to adjust the polymerisation catalyst activity to give the desired polymer properties. Suitably, where one or more active sites need a co-catalyst, the co-catalyst or co-catalysts may be added at different times and in different orders of addition to obtain different products.

The polymerisation reaction may suitably be carried out using solution polymerisation, slurry polymerisation or gas phase polymerisation techniques. Methods and apparatus for effecting such polymerisation reactions are well known and described in, for example, Encyclopaedia of Polymer Science and Engineering published by John Wiley and Sons, 1987, Volume 7, pages 480 to 488 and 1988, Volume 12, pages 504 to 541. The catalysts according to the present invention can be used in similar amounts and under similar conditions to known olefin polymerisation catalysts.

The polymerisation may optionally be carried out in the presence of hydrogen. Hydrogen or other suitable chain transfer agents may be employed in the polymerisation to control the molecular weight of the produced polyolefin. The amount of hydrogen may be such that the percentage of the partial pressure of hydrogen to that of olefin(s) is from 0.001–200%, preferably from 0.01–50%.

Typically, the temperature is from 30 to 110° C. for the slurry or "particle form" process or for the gas phase process. For the solution process the temperature is typically from 100° to 250° C. The pressure used can be selected from a relatively wide range of suitable pressures, e.g. from subatmospheric to about 350 MPa. Suitably, the pressure is from atmospheric to about 6.9 MPa, but may be from 0.05–10, especially 0.14 to 5.5 MPa. In the slurry or particle form process the process is suitably performed with a liquid inert diluent such as a saturated aliphatic hydrocarbon. Suitably the hydrocarbon is a $C_4$ to $C_{10}$ hydrocarbon, e.g. isobutane or an aromatic hydrocarbon liquid such as benzene, toluene or xylene. The polymer is recovered directly from the gas phase process or by filtration or evaporation from the slurry process or evaporation from the solution process.

The invention also includes polymers obtainable by a process using a catalyst according to the present invention.

Melt Index Measurement

The Melt Index (MI) of the polymers produced was determined according to ASTM D1238 Condition E, 2.16 kg at 190° C. while the High Load Melt Index (HLMI) was according to ASTM D1238 condition F, 21.6 kg at 190° C.

Method for Measuring the Molecular Weight Distribution

The molecular weight distribution of a (co)polymer is calculated according to the ratio of the weight-average molecular weight, Mw, to the number-average molecular weight distribution curve obtained by means of a "WATERS" (trademark) model "150 C" gel permeation chromatograph (High Temperature Size Exclusion Chromatograph), the operating conditions being the following:

solvent: 1,2,4-trichlorobenzene;

solvent flow rate: 1.0 ml/minute;

three "SHODEX" (trademark) model "AT 80 MS" columns of 25 cm length are employed;

temperature: 145° C.;

sample concentration: 0.1% by weight;

injection volume: 500 microlitres;

Universal standardisation using monodisperse polystyrene fractions.

The present invention will now be further illustrated with reference to the following examples:

All of the reactions and purifications detailed below involving organometallic species were carried out under a dry nitrogen atmosphere using standard vacuum-line techniques. Tetrahydrofuran and diethyl ether were dried over sodium benzophenone ketyl and distilled. Toluene and alkanes were dried over sodium-potassium and distilled. Dichloromethane was dried over 4 Å molecular sieves. All other reagents were used as received.

EXAMPLE 1:

Preparation of Bis(methoxyethylcyclopentadienyl) Zirconium Dichloride (a) Methoxyethyl Tosylate To a solution of 100 g (525 mmol) p-toluenesulphonyl chloride in 200 ml of dry pyridine cooled to 0° C. was slowly added 19.8 g (260 mmol) 2-methoxyethanol. The reaction solution was thoroughly mixed and allowed to stand in a refrigerator at −5° C. overnight. The reaction mixture was then poured with stirring into 800 g of ice/water. The oily tosylate produced was taken up in 500 ml of diethyl ether and the aqueous layer extracted twice with 500 ml aliquots of diethyl ether. The combined ethereal fractions were washed twice with 500 ml of cold 1:1 hydrochloric acid to remove pyridine and then with 500 ml water, dried over potassium carbonate and magnesium sulphate and decolourised with activated carbon. The solution was filtered and the ether removed under reduced pressure to give a pale yellow oil. The oil was washed several times with petroleum ether and dried under vacuum to give a spectroscopically ($^1$H NMR) pure product (19.7 g, 85.7 mmol, yield =32.9%).

(b) 2-methoxyethylcyclopentadiene

To a solution of 19.7 g (85.7 mmol) 2-methoxyethyltosylate as prepared in step (a) in 200 ml THF cooled to 0° C. was added 55 ml of 2.0M (110 mmol) sodium cyclopentadienylide in THF. The reaction mixture was allowed to warm to room temperature and was stirred for 16 h. 100 ml concentrated aqueous saline solution was added and the product extracted with diethyl ether (3×75 ml). The combined organic fractions were dried over sodium sulphate for 16 hrs, filtered and the solvents removed under reduced pressure using a rotary evaporator to yield a brown oil. The crude product was distilled under reduced pressure (b.p. 40–°44° C. at 2–3 mm Hg) to give 4.5 g of a colourless oil (37.7 mmol, 44.0%).

(C) Bis(2-methoxyethylcyclopentadienyl) Zirconium Dichloride

A solution of 4.5 g (37.7 mmol) 2-methoxyethylcyclopentadiene in 50 ml THF was added to 2.20 g (58.0 mmol) clean, dry potassium metal under nitrogen. This was stirred for two hours at room temperature and warmed to 40 20 C. for a further two hours. After cooling, the solution was filtered and the remaining potassium washed, dried and weighed. The yield of potassium 2-methoxyethylcyclopentadienylide (KCp*) was calculated to be 4.20 g (26.4 mmol). The KCp* solution was added to a slurry of 3.03 g (13.0 mmol) zirconium tetrachloride in 20 ml THF and stirred for two hours. Approximately 0.5 ml water was added to the reaction vessel and the volatiles removed under reduced pressure. The residue was extracted with diethyl ether and filtered. The volume of ether was reduced under vacuum until precipitation began. Cooling to −50° C. in a low temperature freezer yielded 3.50 g of product as colourless needles (8.58 mmol, 66.0%), shown to be spectroscopically pure by $^1$H NMR.

EXAMPLE 2:

Preparation of Bis(2-tetrahydrofurfurylcyclopentadienyl) Zirconium Dichloride (a) Tetrahydrofurfuryltosylate To a solution of 100 g (525 mmol) p-toluenesulphonyl chloride in 200 ml of dry pyridine cooled to 0° C. was slowly added 25 g (245 mmol) tetrahydrofurfurylalcohol. The reaction solution was thoroughly mixed and allowed to stand in a refrigerator at −5° C. overnight. The reaction mixture was then poured with stirring into 1200 g of ice/water. The oily tosylate produced was taken up in 300 ml of diethyl ether and the aqueous layer extracted twice with 300 ml aliquots of diethyl ether. The combined ethereal fractions were washed twice with 300 ml of cold 1:1 hydrochloric acid to remove pyridine and then with 300 ml water, dried over potassium carbonate and sodium sulphate and decolourised with activated carbon. The solution was filtered and the ether removed under reduced pressure to give the product as white crystalline flakes. These were washed several times with hexane and dried under vacuum to yield 54.5 g spectroscopically ($^1$H NMR) pure product (213 mmol, 86.0%).

(b) Tetrahydrofurfurylcyclopentadiene

To a solution of 26.0 g (101 mmol) tetrahydrofurfurylto-sylate prepared according to step (a) above in 200 ml THF cooled to 0° C. was added 63 ml of 2.0M (126 mmol) sodium cyclopentadienylide in THF. The reaction mixture was allowed to warm to room temperature and was stirred for 16 h. 100 ml concentrated aqueous saline solution was then added to the mixture and the product extracted with diethyl ether (3×75 ml). The combined organic fractions were dried over sodium sulphate for 16 h, filtered and the solvents removed under reduced pressure using a rotary evaporator to yield a brown oil. The crude product was distilled under reduced pressure (b.p. 32–°34° C. at 0.3–0.4 mm Hg) to give 7.1 g of a colourless oil (47.3 mmol, 46.9%).

(c) Bis(2-tetrahydrofurfuryl-cyclopentadienyl) Zirconium Dichloride

A solution of 7.0 g (46.7 mmol) tetrahydrofurfurylcyclopentadiene prepared according to step (b) above in 50 ml THF was added to 1.82 g (46.5 mmol) clean, dry potassium metal under nitrogen. This was stirred for two hours at room temperature and was then warmed to 40° C. for a further two hours. After cooling, the solution was filtered and the remaining potassium washed, dried and weighed. The yield of potassium tetrahydrofurfuryl-cyclopentadienylide (KCp') was calculated to be 6.26 g (33.3 mmol). The KCp ' solution was added to 3.73 g (16.0 mmol) zirconium tetrachloride in 20 ml THF and stirred for two hours. Approximately 0.5 ml water was added to the reaction vessel and the volatiles removed under reduced pressure. The residue was extracted with diethyl ether and filtered. The volume of ether was reduced under vacuum until precipitation began. Cooling to −50° C. in a low temperature freezer yielded 4.50 g (9.78 mmol, 61.1%) of product as colourless needles shown to be spectroscopically pure by $^1$H NMR.

EXAMPLE 3:

Preparation of Bis(tetrahydro-3-furanmethylcyclo-pentadienyl) Zirconium Dichloride (a) Tetrahydro-3-furanmethyltosylate To a solution of 100 g (525 mmol) p-toluenesulphonyl chloride in 200 ml dry pyridine cooled to 0° C. was slowly added 25 g (245 mmol) tetrahydro-3-furanmethanol. The reaction solution was thoroughly mixed and allowed to stand in a refrigerator at −5° C. overnight. The reaction mixture was then poured with stirring into 1200 g of ice/water. The oily tosylate produced was taken up in 300 ml of diethyl ether and the aqueous layer extracted twice with 300 ml aliquots of diethyl ether. The combined ethereal fractions were washed twice with 300 ml of cold 1:1 hydrochloric acid to remove pyridine and then with 300 ml water, dried over potassium carbonate and sodium sulphate and decolourised with activated carbon. The solution was filtered and the ether removed on a rotary evaporator. The light-yellow oily residue was repeatedly extracted with pentane (4×500 ml aliquots) with spectroscopically pure product ($^1$H NMR) precipitated from the solutions as a white solid on rapid cooling to −78° C. (combined yield =35.0 g, 137 mmol, 55.9%).

(b) Tetrahydro-3-furanmethylcyclopentadiene

To a solution of 26.0 g (101 mmol) tetrahydro-3-furanmethyl-tosylate prepared according to step (a) above in 200 ml THF cooled to 0° C. was added 63 ml of 2.0M (126 mmol) sodium cyclopentadienylide in THF. The reaction mixture was allowed to warm to room temperature and was stirred for 16 h. 100 ml concentrated aqueous saline solution was added and the product extracted with diethyl ether (3×75 ml). The combined organic fractions were dried over sodium sulphate for 16 hrs, filtered and the solvents removed under reduced pressure to give a brown oil. The crude product was distilled under reduced pressure (b.p. 49–°52° C. at 0.3–0.4 mm Hg) to give 6.35 g of colourless oil (42.3 mmol, 41.9%).

(c) Bis(tetrahydro-3-furanmethylcyclopentadienyl) Zirconium Dichloride

A solution of 6.30 g (42.0 mmol) tetrahydro-3-furanmethyl-cyclopentadiene prepared according to step 2(c) above in 50 ml THF was added to 1.65 g (43.0 mmol) clean, dry potassium metal under nitrogen. The reaction mixture was stirred for two hours at room temperature and then warmed to 40° C. for a further two hours. After cooling, the solution was filtered and the remaining potassium washed, dried and weighed. The yield of potassium tetrahydro-3-furanmethyl-cyclopentadienylide (KCp") was calculated to be 4.91 g (26.1 mmol). The KCp" solution was added to a slurry of 3.04 g (13.0 mmol) zirconium tetrachloride in 20 ml THF and stirred for two hours. Approximately 0.5 ml water was added to the reaction Schlenk tube and then the volatiles were removed under reduced pressure. The residue was extracted with ether and filtered. The volume of ether was reduced under vacuum until precipitation commenced. Cooling to −50° C. in a low temperature freezer yielded 1.95 g of product (4.24 mmol, 32.6%) as colourless needles, spectroscopically pure by $^1$H NMR.

EXAMPLE 4:

Preparation of Silica Supported Ziegler Catalyst 2 g of silica (Crosfield Grade EP10; dried in flowing dry nitrogen at 500° C.) was slurried with n-heptane (10 ml). 10 ml of butylmagnesium chloride solution (2M in diethylether) was added dropwise with stirring. The resulting mixture was stirred at room temperature, for one hour, filtered and washed with 10 ml of n-heptane. Filtration and washing was repeated and the solid then pumped free of solvent. The solid was then re-slurried with n-heptane (10 ml) and 5 ml of titanium tetrachloride solution (1M in toluene) added dropwise with stirring. The mixture was then stirred for one hour at room temperature, filtered, washed and pumped free of solvent as detailed previously.

EXAMPLE 5:

Preparation of Metallocene Complex Supported on a Silica Supported Ziegler Catalyst The product of Example 4 was slurried in 5 ml of toluene. To this slurry was added 10 ml of bis(tetrahydro-3-furanmethylcyclopentadienyl) zirconium dichloride prepared according to Example 3 (0.092 g metallocene in 10 ml toluene). The mixture was stirred at room temperature for one hour then filtered and washed with toluene (10 ml). Filtration and washing was repeated twice. The resulting solid was pumped free of solvent.

EXAMPLE 6:

Preparation of Methyl Aluminoxane (MAO)

To 45.0 g (71 mmol) of finely ground aluminium sulphate hydrate dispersed in 300 ml toluene cooled to 0° C. was slowly added 400 ml of 2.0M (0.8 mol) trimethylaluminium in toluene. The reaction mixture was stirred for 12 hours at ambient temperature and then for four hours at 40° C., after which time the observed evolution of methane gas was negligible. The cooled MAO solution was then filtered into a storage vessel from which aliquots were transferred by cannula as required. The concentration of MAO was calculated to be 24 mg/ml (36.3% yield) by weighing the residue obtained upon removal of volatiles under vacuum from a small sample of the solution.

EXAMPLE 7:

Polymerisation of Ethylene

The reaction was carried out in 3-litre autoclave reactor which was operated under constant pressure conditions. A supported metallocene complex prepared according to any of the examples described herein and methylaluminoxane prepared according to Example 6 in toluene solution were charged to the purged reactor (Al/Zr 1200:1 molar ratio). 1.5 litres of isobutane (research grade) were added with the required amount of hydrogen. The temperature of the reactor was raised to 75° C. and ethylene added to maintain a constant total pressure of 400 psi. The reaction was allowed to continue with stirring at 600 rpm for approximately one hour. The ethylene flow was then terminated and the reactor vented to atmospheric pressure. The polymer was isolated, washed with methanol and vacuum dried.

Comparative Example 1

The process of Example 7 was repeated using only the silica supported Ziegler catalyst prepared according to Example 4.

EXAMPLE 8

Preparation of Metallocene Complex Supported on a Silica Supported Ziegler Catalyst The procedure of Example 5 was followed, except that 0.259 g of metallocene was used.

EXAMPLE 9

Preparation of Metallocene Complex Supported on a Silica Supported Ziegler Catalyst The procedure of Example 5 was followed, except that 0.576 g of metallocene was used.

The Analysis of the resulting polymers prepared in the above examples are given in the accompanying Table.

EXAMPLE 10

Preparation and Ethylene Polymerisation with Silica Supported Metallocene Catalyst 1.97 g silica (Crosfield grade EP10, heated to 800° C. in flowing nitrogen for 6 h) was slurried in heptane (50 ml). To this was added diethylaluminium chloride solution (1M in hexane, 2.4 ml) dropwise at 20° C. with stirring. After 1 h the slurry was filtered and the residue washed with heptane (50 ml), followed by filtration. This was repeated twice more, then the residue was slurried in toluene (50 ml). To this was added bis(tetrahydro-3-furanmethylcyclopentadienyl) zirconium dichloride solution (0.19 g metallocene in 10 ml toluene) dropwise at 20° C. with stirring. After 1.5 h the slurry was filtered and washed using toluene, following the procedure above, then traces of solvent were removed under vacuum at 20° C. to leave a free-flowing solid, 1.24% w/w Zr.

Ethylene polymerisation was carried out as in Example 7, using a hydrogen partial pressure of 20 psi and an Al/Zr ratio of 1825, to give an activity of 384 gPE/mmolZr.h.bar. The polymer was low molecular weight and narrow polydispersity (Mw 3700, PD 4.1). Polymerisation at 1.7 psi hydrogen and an Al/Zr ratio of 1200 gave an activity of 312 gPE/mmolZr.h.bar (Mw 79000, PD 4.1).

TABLE 1

| Catalyst Example | H$_2$ Partial Pressure/psi | Activity gPE/mmol Metal.h.bar | HLMI | MI | MIR |
|---|---|---|---|---|---|
| 5 | 20 | 41 | 2.92 | 0.10 | 29 |
| 8 | 20 | 87 | 3.43 | 0.09 | 38 |
| 9 | 20 | 147 | 19.8 | 0.24 | 83 |
| CE1 | 20 | 106 | 3.34 | 0.11 | 31 |
| 9 | 100 | 98 | 164.7 | 1.39 | 119 |
| CE1 | 100 | 59 | 18.4 | 0.5 | 37 |
| 5 | 1.7 | 119 | * | * | — |
| 9 | 1.7 | 320 | 0.47 | 0.01 | 47 |
| 9 | 50 | 92 | 20.9 | 0.39 | 53 |
| 8[1] | 20 | 63 | 0.12 | * | — |
| 8[1] | 100 | 85 | 1.36 | 0.03 | 45 |
| 9[1] | 20 | 395 | 25 | 0.04 | 625 |

*Too low for measurement

NB. Polymerisations carried out as described in Example 7 except for entries marked [1] in which the Al/Zr was 7200:1.

I claim:

1. A catalyst composition for use in the polymerization of olefins comprising a metallocene complex of the general formula $$M[X(R)_n]_xY_p \qquad (I)$$

wherein M is zirconium, X is a cyclopentadienyl group, R is a radical having Lewis acid functionality selected from the group consisting of an alkoxyl alkyl radical, an heterocyclic oxygen radical or an alkyl heterocyclic oxygen radical, Y is chloride, n is 1 or 5, x is 2, and p is 2, bound to and supported on an inorganic support.

2. A catalyst composition according to claim 1 in which the support is selected from the group consisting of silica, alumina, and Group IIA metal halides.

3. A catalyst composition according to claim 1 supported on said support impregnated with a Lewis acid.

4. A catalyst according to claim 3 in which the Lewis acid is selected from the group consisting of Group VA halides, Group VIA halides, Group IIIB halides, Group IVB halides, Group VB halides, and hydrocarbyl halides.

5. A catalyst composition according to claim 1 supported on an inorganic support which has polymerisation activity.

6. A catalyst composition according to claim 5 in which the support is a Ziegler catalyst.

7. A catalyst composition according to claim 1 mixed with a co-catalyst.

8. A catalyst composition according to claim 7 in which the co-catalyst is an organo aluminium compound.

9. A catalyst composition as defined in claim 1 wherein R is tetrahydrofuryl or tetrahydrofuran alkyl.

10. A catalyst composition as defined in claim 1 wherein said heterocyclic oxygen radical is a five membered ring.

11. A catalyst composition as defined in claim 1 wherein said metallocene complex is bis(2-tetrahydrofurfuryl cyclopentadienyl) zirconium dichloride.

12. A catalyst composition as defined in claim 1 wherein said metallocene complex is bis(methoxyethyl cyclopentadienyl) zirconium dichloride.

13. A metallocene complex having the formula:

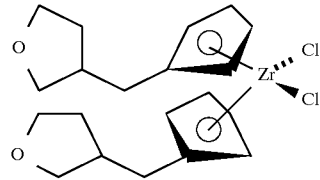

14. A catalyst composition comprising bis(tetrahydro-3-furanmethyl cyclopentadienyl) zirconium dichloride bound to and supported on an inorganic support.

15. A catalyst composition for use in the polymerization of olefins comprising a metallocene complex of the general formula $$M[X(R)_n]_xY_p \qquad (I)$$

wherein M is zirconium, X is a cyclopentadienyl group, R is a methoxyethyl, tetrahydrofuranmethyl, or tetrahydrofurfuryl radical, Y is chloride, n is 1 or 5, x is 2, and p is 2, bound to and supported on an inorganic support.

* * * * *

UNITED STATES PATENT AND TRADEMARK OFFICE
CERTIFICATE OF CORRECTION

PATENT NO. : 5,814,574

DATED : September 29, 1998

INVENTOR(S) : JOHN PAUL McNALLY

It is certified that error appears in the above-identified patent and that said Letters Patent is hereby corrected as shown below:

On the title page,
item [57], ABSTRACT, at far right of second formula, insert --(II)--; first line after formulas, "of" should read --or--; fourth line after formulas, "lewis" should be --Lewis--.

Column 1, line 35, insert --(II)-- at far right of second formula.

Column 1, line 40, "-20C" should read --1-20C--.

Column 8, line 14, "40 20 C." should read --40° C.--; line 33, "To a solution..." should be the start of a new paragraph; line 62, "32-°34°" should be --32-34°--.

Column 9, line 50, "49-°52°" should be --49-52°--.

Signed and Sealed this

Sixteenth Day of March, 1999

Attest:

Q. TODD DICKINSON

*Attesting Officer*     *Acting Commissioner of Patents and Trademarks*